United States Patent

Gasc et al.

[11] 4,242,331
[45] Dec. 30, 1980

[54] AMINOGLYCOSIDES AND METHOD OF USE

[75] Inventors: Jean-Claude Gasc, Bondy; Claude Rettien, Montreuil, both of France

[73] Assignee: Roussel Uclaf, Paris, France

[21] Appl. No.: 67,316

[22] Filed: Aug. 17, 1979

[30] Foreign Application Priority Data

Sep. 6, 1978 [FR] France .................. 78 25604

[51] Int. Cl.³ ............... A61K 31/71; C07H 15/22
[52] U.S. Cl. ............................ 424/180; 536/4; 536/10; 536/17 R
[58] Field of Search .................. 424/180; 536/17 R

[56] References Cited

U.S. PATENT DOCUMENTS

| | | | |
|---|---|---|---|
| 4,001,208 | 1/1977 | Umezawa et al. | 536/17 R |
| 4,031,210 | 6/1977 | Chazan et al. | 536/17 R |
| 4,117,221 | 9/1978 | Daniels | 536/17 R |
| 4,146,617 | 3/1979 | Chazan et al. | 536/17 R |

Primary Examiner—Johnnie R. Brown
Attorney, Agent, or Firm—Hammond & Littell, Weissenberger and Muserlian

[57] ABSTRACT

Novel aminoglycoside derivatives of desoxystreptamines of the formula

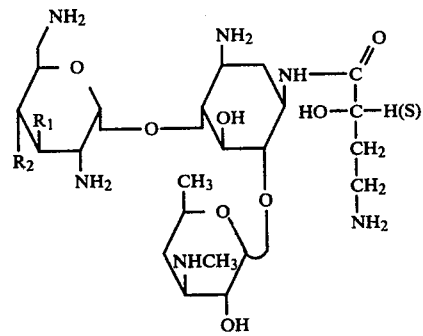

wherein $R_1$ and $R_2$ are selected from the group consisting of hydrogen and hydroxyl with at least one of them being hydrogen and their non-toxic, pharmaceutically acceptable acid addition salts having antibiotic properties and their preparation.

13 Claims, No Drawings

AMINOGLYCOSIDES AND METHOD OF USE

STATE OF THE ART

Related compounds are described in French Pat. Nos. 2,358,156 and 2,351,660 and commonly assigned U.S. patent application Ser. No. 705,576 filed on July 15, 1976, now abandoned.

OBJECTS OF THE INVENTION

It is an object of the invention to provide the novel aminoglycosides of formula I and their non-toxic, pharmaceutically acceptable acid addition salts and a novel process and novel intermediates for their preparation.

It is another object of the invention to provide novel antibiotic compositions and a novel method of combatting bacterial infections in warm-blooded animals.

These and other objects and advantages of the invention will become obvious from the following detailed description.

THE INVENTION

The novel aminoglycosides of the invention are selected from the group consisting of desoxystreptamines of the formula

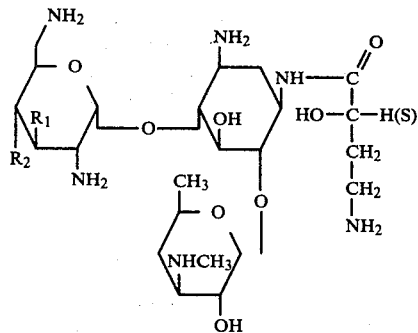

wherein $R_1$ and $R_2$ are selected from the group consisting of hydrogen and hydroxyl with at least one of them being hydrogen and their non-toxic, pharmaceutically acceptable acid addition salts. The symbol (S) expresses a steric configuration of organic compounds as defined by Cahn et al [Experientia, Vol. 12 (1956), p. 81–94].

Preferred compounds of formula I and their salts are 1′-O-[2,6-diamino-2,3,6-tridesoxy-α,D-ribohexopyranosyl-(1→4)]-O-[3-methylamino-3,4,6-tridesoxy-α,D-xylohexopyranosyl-(1→6)]-N¹-[2(S)-hydroxy-1-oxo-4-amino]butyl-2-desoxy-D-streptamine and its sulfate, 1′-O-[2,6-diamino-2,4,6-tridesoxy-α,D-xylohexopyranosyl-(1→4)]-O-[3-methylamino-3,4,6-tridesoxy-α,D-xylohexopyranosyl-(1→6)]-N¹-[2(S)-hydroxy-1-oxo-4-amino]butyl-2-desoxy-D-streptamine and its sulfate and 1′-O-[2,6-diamino-2,3,4,6-tetradesoxy-α,D-erthrohexopyranosyl-(1→4)]-O-[3-methylamino-3,4,6-tridesoxy-α,D-xylohexopyranosyl)-(1→6)]-N¹-[2(S)-hydroxy-1-oxo-4-amino]butyl-2-desoxy-D-streptamine and its sulfate.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, benzoic acid, maleic acid, fumaric acid, succinic acid, tartaric acid, citric acid, oxalic acid, benzylic acid, glyoxylic acid, aspartic acid, alkane sulfonic acids and arylsulfonic acids.

The novel process of the invention for the preparation of compounds of formula I comprises reacting a compound of the formula

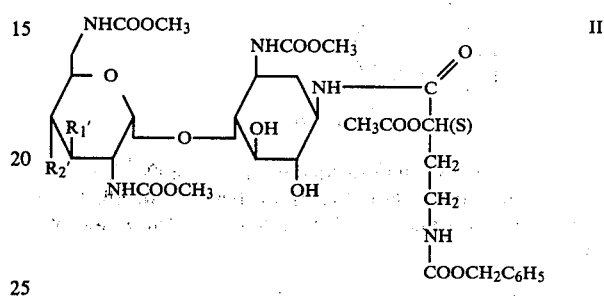

wherein $R_1'$ and $R_2'$ are selected from the group consisting of hydrogen and benzoxy with at least one being hydrogen with a compound of the formula

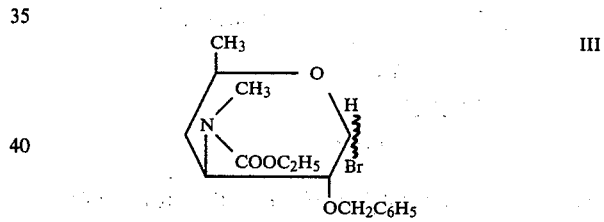

in the presence of an alkaline agent to obtain a mixture of α and β anomeres of the formulae

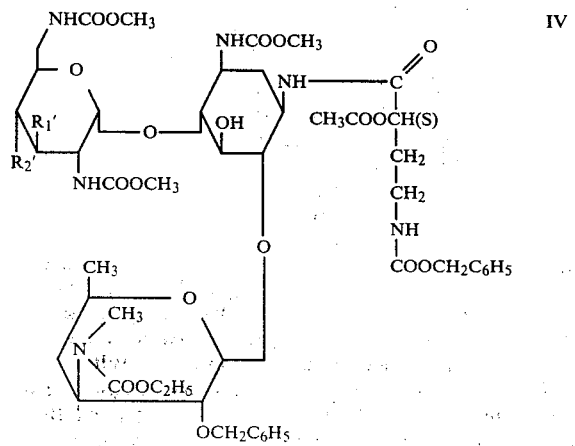

-continued

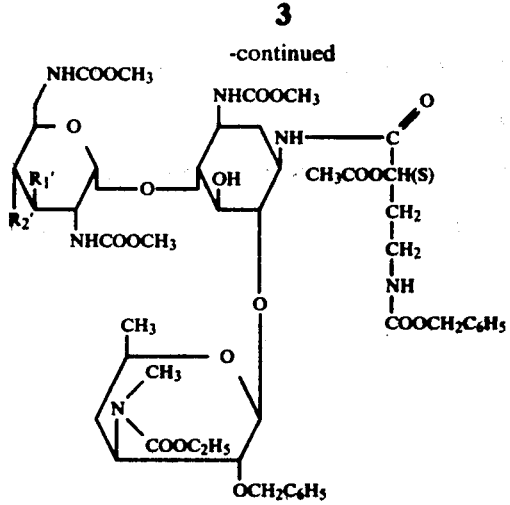

recovering the product of formula IV from the mixture and subjecting the latter to hydrolysis in an alkaline medium in an organic solvent to obtain a compound of the formula

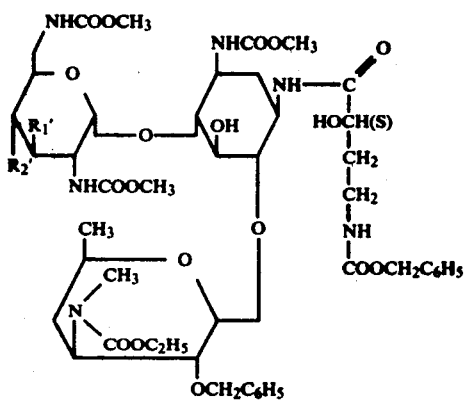

reacting the latter with hydrogen in the presence of a catayst to obtain a compound of the formula

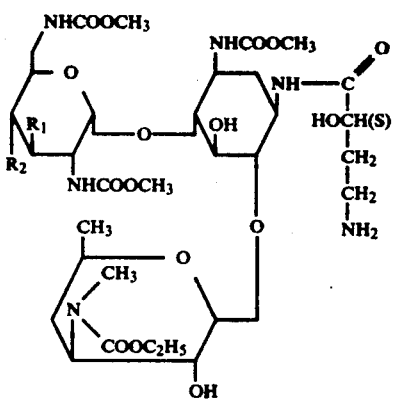

wherein $R_1$ and $R_2$ have the above definition and subjecting the latter to hydrolysis in an alkaline medium to obtain a compound of formula I which may be salified with an organic or inorganic acid to form the non-toxic, pharmaceutically acceptable acid addition salt.

The preferred alkaline agent for the reaction of the compounds of formulae II and III is diisopropylethylamine but other tertiary bases such as triethylamine may be used. The reaction is effected in the presence of a tetraloweralkyl quaternary ammonium base such as tetraethyl ammonium bromide in an organic solvent such as dichloroethane or dimethylformamide, but preferably methylene chloride.

The separation of the compound of formulae IV and IV may be effected by known methods, preferably by chromatography over silica gel although equally useful is chromatography with alumina, cellulose or magnesium silicate or by fractional crystallization or countercurrent extraction. For these separations, different solvents or mixtures of aqueous or pure organic solvents may be used.

The alkaline agent for the hydrolysis of the compound of formula IV is preferably sodium hydroxide but also useful are potassium hydroxide, lithium hydroxide or barium hydroxide and the organic solvent is preferably a mixture of an alkanol such as ethanol or methanol and methylene chloride or dimethylformamide. The hydrogenation catalyst is preferably palladium but other catalysts such as Raney nickel, palladium salts or platinum derivatives may be used and the preferred solvent is an aqueous acid solvent such as a mixture of acetic acid or propionic acid and water.

The alkaline agent for the hydrolysis of a compound of formula VI is preferably potassium hydroxide but also useful is sodium hydroxide. The salification of the compounds of formula I may be effected by usual methods by total or partial neutralisation of the five amine functions of the products of formula I with the desired acid in a solvent or mixture of solvents such as water, ether, methanol or acetone.

The wavy line indicating the substituents on the carbon atom in the 1-position of the ring of compounds of formula III indicates that the substituents may be in the α- or β-positions of the ring and the compound may be in the form of its α- or β-anomeres or mixtures thereof.

The novel anitibiotic compositions of the invention are comprised of an antibiotically effective amount of a least one compound of formula I and its non-toxic, pharmaceutically acceptable acid addition salts and an inert pharmaceutical carrier or excipient. The compositions may be in the form of tablets, dragees, gelules, granules, suppositories, injectable solutions or suspensions, pomades, cremes or gels.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions of the invention possess a very interesting antibiotic activity against both gram positive bacteria such as staphylococcus, streptococcus and especially penicillin resistant staphylococcus and gram negative bacteria, especially coliform bacteria and Klebsiella. The compositions therefore are useful for the treatment of staphylococcia such as *staphylococcal septicemia*, staphylococcia malignant on the face, cutaneous staphylococcia, pyodermatitis, septic or suppurantes sores, anthrax, phlegmons, eresipels, acute primitive or post-influenza staphylococcia, bronchopneumonia, pulmonary suppurations or collibacillosis. They are also useful for treating infections of Klebsiella, Enterobacter and Pseudomonas.

The novel method of the invention for treating bacterial infections in warm-blooded animals, including humans, comprises administering to warm-blooded animals a bactericidally effective amount of at least one compound of formula I or a non-toxic, pharmaceutically acceptable acid addition salt thereof. The compounds may be administered orally, rectally, parenterally or topically to the skin or mucous membrane. The usual daily dose is depending on the compound and the method of administration. It may be a 2 mg to 20 mg/kg per day with the product of example 2 when administered parenterally.

The novel intermediates of the invention include the compounds of formulae IV, V and VI.

The starting compounds of formula II may be prepared by the process of French Pat. No. 2,202,078 and the compounds of formula III may be prepared by treating 1-0-acetyl-2-0-benzyl-3-(N-carbethoxy-N-methyl)-amino-3,4,6-tridesoxy-D-xylohexopyranose described in French Pat. No. 2,290,908 with hydrobromic acid.

In the following examples there are described several preferred embodiments to illustrate the invention. However, it is to be understood that the invention is not intended to be limited to the specific embodiments.

EXAMPLE 1

0-[2,6-diamino-2,3,6-tridesoxy-α,D-ribohexopyranosyl-(1→4)]-0-[3-methylamino-3,4,6-tridesoxy-α,D-xylohexopyranosyl-(1→6)]-$N^1$-(4-amino-2(S)-hydroxy-1-oxo)-butyl-2-desoxy-D-streptamine

STEP A:

2-desoxy-4-0-[2,3,6-tridesoxy-2,6-bis-[(methoxycarbonyl)-amino]-α,D-ribohexopyranosyl]-5,6-0-(1-methyl)-ethylidene-$N^1$-$N^3$-bismethoxycarbonyl-D-streptamine 20 ml of dimethoxypropane and 200 mg of p-toluene sulfonic acid were added to a solution of 38.5 g of 4'-acetyl-3'-desoxy-tetra-N-carbomethoxy-neamine (prepared as in French Pat. No. 2,290,908) in 155 ml of dimethylformamide and the solution was stirred under an inert atmosphere while heating in a water bath at 90° C. for 17 hours. Another 20 ml of dimethoxypropane and 200 mg of p-toluene sulfonic acid were added thereto and the mixture was stirred at 90° C. for another 25 hours. A further 20 ml of dimethoxypropane and 200 mg of p-toluene sulfonic acid were added to the mixture and the mixture was stirred at 110° C. for 24 hours. A fourth portion of 20 ml of dimethoxypropane and 200 mg of p-toluene sulfonic acid were added to the mixture which was stirred at 110° C. for 30 hours and was then cooled. Dowex 1×2 ion exchange resin (OH$^-$ 50/100 mesh) was added to the mixture to obtain an alkaline pH and the mixture was filtered. The filtrate was evaporated to dryness to obtain 45.6 g of residue and 44.6 g of the residue were dissolved in 90 ml of methanol and the solution was cooled to 0° C. 90 ml of sodium hydroxide solutions were added dropwise to the solution and the mixture was extracted with essence B (b.p.=60°–80° C.) and with chloroform and the combined extracts were dried and evaporated to dryness to obtain 33.10 g of 2-desoxy-4-0-[2,3,6-tridesoxy-2,6-bis-[(methoxycarbonyl)-amino]-α,D-ribohexopyranosyl]-5,6-0-(1-methyl)-ethylidene-$N^1$-$N^3$-bismethoxycarbonyl-D-streptamine in the form of an amorphus beige powder. Thin layer chromatography over silica gel and elution with a 9-1 chloroform-methanol mixture yielded an Rf=0.40.

STEP B:

2-desoxy-4-0-[2,3,6-tridesoxy-2,6-bis[(methoxycarbonyl)-amino]-4-0-benzyl-α,D-ribohexopyranosyl]-5,6-0-(1-methyl)-ethylidene-$N^1$-$N^3$-bismethoxycarbonyl-D-streptamine 17.0 g of barium oxide, 25.6 g of barium hydroxide octahydrate and 25.6 ml of benzyl bromide were added to an iced solution of 25.6 g of the product of Step A in 85 ml of dimethoxyformamide and after warming the mixture was stirred for 24 hours and was poured into water. The mixture was extracted with benzene and the organic phase was dried and evaporated to dryness to obtain 36.0 g of residue. The residue was chromatographed over silica gel and was eluted with a 98-2 chloroform-methanol mixture to obtain 7.614 g of pure 2-desoxy-4-0-[2,3,6-tridesoxy-2,6-bis-[(methoxycarbonyl)-amino]-4-0-benzyl-α,D-ribohexopyranosyl]-5,6-0-(1-methyl)-ethylidene-$N^1$-$N^3$-bismethoxycarbonyl-D-streptamine in the form of an amorphorus beige spongy mass. Thin-layer chromatography over silica gel and elution with 95-5 chloroform-methanol mixture yielded an Rf=0.36.

STEP C:

2-desoxy-4-0-[2,3,6-tridesoxy-2,6-bis-[(methoxycarbonyl)-amino]-4-0-benzyl-α,D-ribohexopyranosyl]-$N^1$-$N^3$-bismethoxycarbonyl-D-streptamine A solution of 7.585 g of the product of Step B in 25 ml of aqueous acetic acid was heated moderately with stirring for one hour and was then poured into water. The mixture was cooled for a few hours at 0° C. and the mixture was vacuum filtered. The recovered crystals were washed and dried to obtain 5.204 g of 2-desoxy-4-0-[,2,3,6-tridesoxy-2,6-bis[(methoxycarbonyl)-amino]-4-0-benzyl-α,D-ribohexopyranosyl]-$N^1$-$N^3$-bismethoxycarbonyl-D-streptamine in the form of white needles melting at 251° C. Thin-layer chromatography over silica gel and elution with a 9-1 chloroform-methanol mixture yielded an Rf=0.29.

STEP D:

1,6-N-O-(carbonyl)-2-desoxy-4-0-[2,3,6-tridesoxy-2,6-bis-[(methoxycarbonyl)-amino]-4-0-benzyl-α,D-ribohexopyranosyl]-$N^3$-methoxycarbonyl-D-streptamine 5.90 ml of tert.-butyl alcohol and 5.3 g of sodium tert.-butylate were added to a solution of 5.900 g of the product of Step C in 118 ml of dimethylformamide cooled to 0° C. and after about 16 hours, the mixture was diluted with dimethylformamide. The mixture was neutralized with 5.9 ml of acetic acid in 5.9 ml of dimethylformamide and the mixture was poured into water. The mixture was extracted with chloroform and the organic phase was dried and evaporated to dryness to obtain 5.719 g of 1,6-N-O-(carbonyl)-2-desoxy-4-0-[2,3,6-tridesoxy-2,6-bis-[(methoxycarbonyl)-amino]-4-0-benzyl-α,D-ribohexopyranosyl]-$N^3$-methoxycarbonyl-D-streptamine in the form of a white amorphus product. Thin-layer chromatography over silica gel and elution with a 9-1 chloroform-methanol mixture yielded an Rf=0.18.

STEP E:
2-desoxy-4-0-[2,3,6-tridesoxy-2,6-bis-[(methoxycarbonyl)-amino]-4-0-benzyl-α,D-ribohexopyranosyl]-N$^3$-methoxycarbonyl-D-streptamine A suspension of 6.638 g of the product of Step D in 89.6 ml of 20 volumes of oxygenated water and 66.3 ml of N sodium hydroxide solution was stirred for 4 hours and was iced. Excess oxygenated water was neutralized with sodium thiosulfate. The pH was adjusted to 7 with sulfuric acid and the mixture was evaporated to dryness. The residue was extracted with a chloroform-methanol mixture and the mixture was filtered. The mineral salts were washed and the filtrate was evaporated to dryness. The residue was chromatographed over silica gel and elution with a 70-30-2 chloroform-methanol-ammonium hydroxide mixture yielded 2.810 g of pure 2-desoxy-4-0-[2,3,6-tridesoxy-2,6-bis-[(methoxycarbonyl)-amino]-4-0-benzyl-α,D-ribohexopyranosyl]-N$^3$-methoxycarbonyl-D-streptamine.
Thin-layer chromatography over silica gel and elution with a 70-30-2 chloroform-methanol-ammonium hydroxide mixture yielded an Rf=0.29.

STEP F: (S)
α-acetyloxy-γ-N-benzyloxycarbonylamido-n-butyric acid

A mixture of 2 ml of acetic acid and a solution of 3 g of (S) α-hydroxy-γ-carbonylbenzylamino-butyric acid (prepared as in French Pat. No. 2,145,649) in 3 ml of pyridine and 10 ml of methylene chloride was stirred for 3 hours and was then diluted with methylene chloride. The mixture was washed, dried and evaporated to dryness to obtain 3.45 g of (S) α-acetyloxy-γ-N-benzyloxycarbonylamido-n-butyric acid in the form of a colorless oil which was used as is for the next step.

STEP G:
2-desoxy-4-0-[2,3,6-tridesoxy-2,6-bis-[(methoxy-carbonyl)-amino]-4-0-benzyl-α,D-ribohexopyranosyl]-N$^1$-{2(S)-acetyloxy-1-oxo-4-[phenylmethoxycarbonyl]-amino}-butyl-N$^3$-methoxycarbonyl-D-streptamine 0.84 ml of triethylamine and 0.516 ml of ethyl chloroformate were added to a solution of 1.785 g of the acid of Step F in 34 ml of anhydrous tetrahydrofuran and the mixture was stirred for one hour. A solution of 2.760 g of the product of Step E in 45 ml of dimethylformamide was added to the mixture which was then stirred for 75 minutes. 100 ml of water were added thereto and the mixture was slowly poured with stirring into 1.6 liters of water. The mixture was iced for 2 hours at 0° C. and was then vacuum filtered. The recovered product was washed and dried to obtain 3.759 g of 2-desoxy-4-0-[2,3,6-tridesoxy-2,6-bis-[(methoxycarbonyl)-amino]-4-0-benzyl-α,D-ribohexopyranosyl]-N$^1$-{2(S)-acetyloxy-1-oxo-4-[phenylmethoxycarbonyl]-amino}-butyl-N$^3$-methoxycarbonyl-D-streptamine. Thin-layer chromatography over silica gel and elution with a 9-1 chloroform-methanol mixture yielded an Rf=0.26.

STEP H:
0-[3-ethoxycarbonylmethylamino)-2-0-benzyl-3,4,6-tridesoxy-α,D-xylohexopyranosyl-(1→6)]-0-[2,3,6-tridesoxy-2,6-bis-[methoxycarbonylamino]-4-0-benzyl-α,D-ribohexopyranosyl-(1→4)]-N$^1$-[2(S)-acetyloxy-1-oxo-4-(benzyloxycarbonylamino]-butyl-2-desoxy-N$^3$-D(methoxycarbonyl)-D-streptamine A solution of 2.4 g of 1-0-acetyl-2-0-benzyl-3-(N-carbethoxy-N-methylamino)-3,4,6-tridesoxy-D-xylohexopyranose in 110 ml of anhydrous methylene chloride saturated with hydrobromic acid was stirred for 45 minutes and was then evaporated to dryness. The residue was taken up in 90 ml of methylene chloride and 1.39 g of tetraethylammonium bromide, 1.19 g of diisopropylethylamine and 3.73 g of the product of Step G were added to the solution. The mixture was refluxed under an inert atmosphere for 4 hours and then 0.5 equivalent of tetraethylammonium bromide and 0.5 equivalent of diisopropylethylamine were added thereto. After 22 hours, the process was repeated and again after 30 hours and after 40 hours of reflux, the mixture was cooled and poured into water. The mixture was extracted with methylene chloride and the organic phase was dried and evaporated to dryness to obtain 8.256 g of residue. The residue was chromatographed over silica gel and was eluted with a 7-3 chloroform-acetone mixture to obtain 3.5 g of the α-anomere of 0-[3-(ethoxycarbonylmethylamino)-2-0-benzyl-3,4,6-tridesoxy-α,D-xylohexopyranosyl-(1→6)]-0-[2,3,6-tridesoxy-2,6-bis-[methoxycarbonylamino]-4-0-benzyl-α,D-ribohexopyranosyl-(1→4)]-N$^1$-[2(S-acetyloxy-1-oxo-4(benzyloxycarbonylamino)]-butyl-2-desoxy-N$^3$-(methoxycarbonyl)-D-streptamine with an Rf=0.30 and the β-anomere of the said compound had an Rf=0.20 under the same conditions.

STEP I.
0-[3-(ethoxycarbonylmethylamino)-2-0-benzyl-3,4,6-tridesoxy-α,D-xylohexopyranosyl-(1→6)]-0-[2,3,6-tridesoxy-2,6-bis-[methoxycarbonylamino]-4-0-benzyl-α,D-ribohexopyranosyl-(1→4)]-N$^1$-[2(S)-hydroxy-1-oxo-4-(benzyloxycarbonylamino)]-butyl-2-desoxy-N$^3$-methoxycarbonyl-D-steptamine 2.25 ml of 2 N sodium hydroxide solution were added to a solution of 3.47 g of the product of Step H in 22.5 ml of methanol and 22.5 ml of methylene chloride cooled to 0° C. and after the mixture was stirred for one hour, it was neutralized with N hydrochloric acid. The organic phase was washed with water and the aqueous phase was washed with methylene chloride. The organic phase was dried and evaporated to dryness. The residue was chromatographed over silica gel and was eluted with a 97-3 chloroform-methanol mixture to obtain 3.116 g of 0-[3-(ethoxycarbonylmethylamino)-2-0-benzyl-3,4,6-tridesoxy-α,D-xylohexopyranosyl-(1→6)]-0-[2,3,6-tridesoxy-2,6-bis-[methoxycarbonylamino]-4-0-benzyl-α,D-ribohexopyranosyl-(1→4)]-N$^1$-[2(S-hydroxy-1-oxo-4-(benzyloxycarbonylamino)]-butyl-2-desoxy-N$^3$-methoxycarbonyl-D-streptamine in the form of a white amorphous product. Thin-layer chromatography and elution with a 95-5 chloroform-methanol mixture yielded an Rf=0.44.

STEP J: Acetate of O-[3-ethoxycarbonylmethylamino-3,4,6-tridesoxy-α,D-xylohexopyranosyl-(1→6)]-O-[2,6-bis-(methoxycarbonylamino)-2,3,6-tridesoxy-α,D-ribohexopyranosyl-(1→4)]-N¹-[2(S)-hydroxy-1-oxo-4-amino]-butyl-2-desoxy-N³-(methoxycarbonyl)-D-streptamine 616 mg of 9.81% palladized carbon were added to a solution of 3.080 g of the product of Step I in 15.4 ml of acetic acid and 15.4 ml of water and hydrogen was bubbled therethrough for 21 hours. The catalyst was removed by filtration and the filter was washed with acetic acid. The filtrate was evaporated to dryness and the residue was dried under reduced pressure with heat to obtain 2.292 g of acetate of O-[3-ethoxycarbonylmethylamino-3,4,6-tridesoxy-α,D-xylohexopyranosyl-(1→6)]-O-[2,6-bis-(methoxycarbonylamino)-2,3,6-tridesoxy-α,D-ribohexopyranosyl-(1→4)]-N¹-[2(S)-hydroxy-1-oxo-4-amino]-butyl-2-desoxy-N³-(methoxycarbonyl)-D-streptamine as a beige amorphous powder. Thin-layer chromatography with a 70-30-2.5 chloroform-methanol-ammonium hydroxide eluant mixture yielded an Rf=0.24.

STEP K-
O-[2,6-diamino-2,3,6-tridesoxy-α,D-ribohexopyranosyl-(1→4)]-O-[3-methylamino-3,4,6-tridesoxy-α,D-xylohexopyranosyl-(1→6)]-N¹-[4-amino-2(S)-hydroxy-1-oxo]-butyl-2-desoxy-D-streptamine A stirred mixture of 2.263 g of the product of Step I and 11.3 ml of 14 N potassium hydroxide solution was heated to 60° C. for 85 minutes and was then cooled to 0° C. and acidified with N sulfuric acid to a pH of 3. The recovered product was chromatographed over a column of IRP 64 ion exchange resin in the ammonium salt form and was eluted with 0.4 N ammonium hydroxide solution to obtain 1.155 g of O-[2,6-diamino-2,3,6-tridesoxy-α,D-ribohexopyranosyl-(1→4)]-O-[3-methylamino-3,4,6-tridesoxy-α,D-xylohexopyranosyl-(1→6)]-N¹-[4-amino-2(S)-hydroxy-1-oxo]-butyl-2-desoxy-D-streptamine. Thin-layer chromatography with an eluant of 2-2-1 chloroform-methanol-ammonium hydroxide yielded an Rf=0.18.

NMR Spectrum (D₂O-DCl-60 MHz):

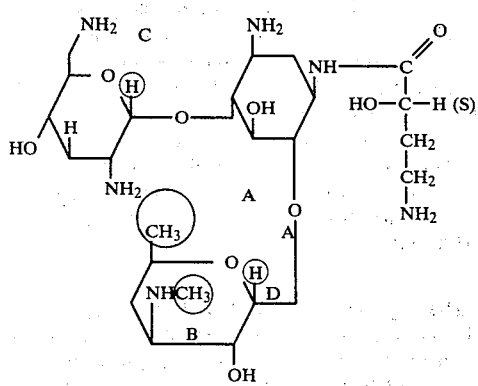

A—CH₃—1.2 ppm doublet J=6
B—CH₃—2.7 ppm
C—H anomere—5.8 ppm doublet J=3.5
D—H anomere—5.2 ppm doublet J=3.0

EXAMPLE 2
O-[2,6-diamino-2,3,6-tridesoxy-α,D-ribohexopyranosyl-(1→4)-O-[3-methylamino-3,4,6-tridesoxy-α,D-xylohexopyranosyl-(1→6)-N¹-[4-amino-2(S)-hydroxy-1-oxo]-butyl-2-desoxy-D-streptamine sulfate An aqueous solution of 1.00 g of the product of Example 1 was acidified to a pH of 3 with sulfuric acid and the solution was concentrated and filtered. The filtrate was concentrated further and was then poured into methanol with stirring. The stirred mixture was iced for a few hours and was then vacuum filtered. The recovered product was washed and dried to obtain 1.4 g of O-[2,6-diamino-2,3,6-tridesoxy-α,D-ribohexopyranosyl-[1→4)]-O-[3-methylamino-3,4,6-tridesoxy-α,D-xylohexopyranosyl-(1→6)]-N¹-[4-amino-2(S)-hydroxy-1-oxo]-butyl-2-desoxy-D-streptamine sulfate in the form of an amorphous white powder. Thin-layer chromatography over silica gel with an eluant of a 2-2-1 chloroform-methanol-ammonium hydroxide mixture yielded an Rf=0.19.

NMR Spectrum (D₂O-60 MHz):

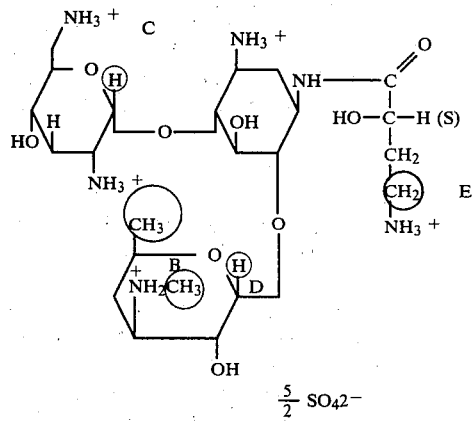

A—1.22 ppm doublet J=6.5
B—2.7 ppm
C—H anomere 5.9 ppm doublet J=3.5
D—H anomere 5.2 ppm doublet J=3.5
E—3.2 ppm triplet J=7

EXAMPLE 3
1'O-[2,6-diamino-2,4,6-tridesoxy-α,D-xylohexopyranosyl-(1→4)]-O-[3-methylamino-3,4,6-tridesoxy-α,D-xylohexopyranosyl-(1→6)]-N¹-[4-amino-2(S)-hydroxy-1-oxo]-butyl-2-desoxy-D-streptamine

STEP A:
5,6-O-cyclohexylidene-4'-O-tosyl-tetra-N-carbomethoxy-neamine

A mixture of 795 g of tosyl chloride and 1590 g of 5,6-cyclohexylidene-tetra-N-carbomethoxy-neamine [J. of Antibiotics, 1971, p. 711] in pyridine was held at 2° C. for one hour and then the temperature was allowed to return to room temperature. The mixture was stirred for 40 hours and then 530 g of potassium formate were added thereto in small fractions. The mixture was stirred for one hour and the gummy extract was dissolved in 2.5 liters of water and 2.5 liters of methylene chloride. The organic phase was washed with water and the aqueous phase was extracted with methylene chloride. The organic phase was dried and evaporated to dryness. The residue was triturated 3 times with isopropyl ether. The organic phase was concentrated to dryness under reduced pressure at 80° C. and the gummy residue was dissolved in 3 liters of methylene chloride. Crystallization was induced and the mixture was filtered. The recovered crystals were washed and dried to obtain 560 g of 5,6-O-cyclohexylidene-4'-O-tosyl-tetra-N-carbomethoxy-neamine with a specific rotation of $[\alpha]_D^{20} = 19° \pm 3°$ (c=0.5% in CHCl$_3$).

STEP B:

5,6-O-cyclohexylidene-2-desoxy-4-O[2,4,6-tridesoxy-4-iodo-2,6,-bis-(methoxycarbonylamino)-α,D-xylohexopyranosyl]-N$^1$,N$^3$-bis-(methoxycarbonyl)-D-streptamine A mixture of 30.3 g of sodium iodide in 130 ml of dimethylformamide was heated to 115° C. and 13.3 g of the product of Step A were added thereto. After 2¼ hours, the mixture was cooled and was poured into water. The mixture was extracted five times with methylene chloride and the combined extracts were dried and evaporated to dryness to obtain 7.843 g of 5,6-O-cyclohexylidene-2-desoxy-4-O-[2,4,6-tridesoxy-4-iodo-2,6-bis-(methoxycarbonylamino)-α,D-xylohexopyranosyl]-N$^1$,N$^3$-bis-(methoxycarbonyl)-D-streptamine in the form of an oil which hardened as a light porous mass. Thin-layer chromatography over silica gel with a 9-1 chloroform-methanol eluant yielded an Rf=0.45.

STEP C:

5,6-O-cyclohexylidene-2-desoxy-4-O-[2,4,6-tridesoxy-2,6-bis-(methoxycarbonyl)-amino-α,D-xylohexopyranosyl]-N$^1$,N$^3$-bis-(methoxycarbonyl)-D-streptamine 7.84 g of the product of Step B were added to a suspension of 35 ml of Raney nickel in 150 ml of ethanol and the mixture was stirred for one hour and was then filtered. The filtrate was evaporated to dryness to obtain 5.17 g of residue in the form of a white porous mass which was purified by chromatography over silica gel to obtain 4.506 g of pure 5,6-O-cyclohexylidene-2-desoxy-4-O-[2,4,6-tridesoxy-2,6-bis-(methoxycarbonyl)-amino-α,D-xylohexopyranosyl]-N$^1$,N$^3$-bis-(methoxycarbonyl)-D-streptamine. Thin-layer chromatography over silica gel with a 9-1 chloroform-methanol eluant yielded an Rf=0.40.

STEP D:

5,6-O-cyclohexylidene-2-desoxy-4-O-[2,4,6-tridesoxy-2,6-bis-(methoxycarbonyl)-amino-3-O-benzyl-α,D-xylohexopyransolyl]-N$^1$,N$^3$-bis-(methoxycarbonyl)-D-streptamine 13.355 g of barium oxide, 13.355 g of baryta and 13.355 g of benzyl bromide were added to an iced solution of 13.355 g of the product of Step C in 53.5 ml of dimethylformamide and the mixture was stirred at 0° C. for 20 hours and was then allowed to warm up. The mixture was stirred for another 5 hours and was then poured into water. The mixture was extracted 5 times with chloroform and the combined extracts were dried and evaporated to dryness. The residue was chromatographed twice over silica gel to obtain 9.279 g of 5,6-O-cyclohexylidene-2-desoxy-4-O-[2,4,6-tridesoxy-2,6-bis-(methoxycarbonyl)-amino-3-O-benzyl-α,D-xylohexopyranosyl]-N$^1$,N$^3$-bis-(methoxycarbonyl)-D-streptamine. Thin-layer chromatography over silica gel with a 95-5 chloroform-methanol eluant yielded an Rf=0.44.

STEP E:

2-desoxy-4-O-[2,4,6-tridesoxy-2,6-bis-(methoxycarbonyl)-amino-3-O-benzyl-α,D-xylohexopyranosyl]-N$^1$,N$^3$-bis-(methoxycarbonyl)-D-streptamine A solution of 10 g of the product of Step D in 30 ml of 80% acetic acid was heated at 60° C. with stirring for 75 minutes and was then cooled and evaporated to dryness to obtain 7.615 g of 2-desoxy-4-O-[2,4,6-tridesoxy-2,6-bis(methoxycarbonyl)-amino-3-O-benzyl-α,D-xylohexopyranosyl]-N$^1$,N$^3$-bis-methoxycarbonyl)-D-streptamine. Thin-layer chromatography over silica gel with a 9-1 chloroform-methanol eluant yielded an Rf=0.25.

STEP F:

1,6-N,O-(carbonyl)-2-desoxy-4-O-[2,4,6-tridesoxy-2,6-bis-(methoxycarbonyl)-amino-3-O-benzyl-α,D-xylohexopyranosyl]-N$^3$-methoxycarbonyl-D-streptamine 7.6 ml of tert.-butanol were added to a solution of 7.6 g of the product of Step E in 150 ml of dimethylformamide and then 6.65 g of potassium tert.-butylate were added to the stirred mixture in an ice bath. The mixture was stirred for 18 hours and was then diluted with dimethylformamide. The mixture was acidified with 7.6 ml of acetic acid in 7.6 ml of dimethylformamide and the mixture was poured into water. The mixture was extracted with methylene chloride and the organic phase was washed with water, dried and evaporated to dryness to obtain 7.145 g of 1,6-N,O-(carbonyl)-2-desoxy-4-O[2,4,6-tridesoxy-2,6-bis-(methoxycarbonyl)-amino-3-O-benzyl-α,D-xylohexopyranosyl]-N$^3$-methoxycarbonyl-D-streptamine. Thin-layer chromatography twice over silica gel with a 9-1 chloroform-methanol eluant yielded an Rf=0.42.

STEP G:

2-desoxy-4-O-[2,4,6-tridesoxy-2,6-bis-(methoxycarbonyl)-amino-3-O-benzyl-α,D-xylohexopyranosyl]-N$^3$-methoxycarbonyl-D-streptamine 45 ml of hydrogen peroxide and 60 ml of sodium hydroxide were added to a solution of 6.170 g of the product of Step F in 10 ml of chloroform and the mixture was stirred for one hour and was iced. Sodium thiosulfate was added to the mixture to neutralize excess hydrogen peroxide and the pH was adjusted to 5 with sulfuric acid. The mixture was extracted with chloroform and the organic phase was evaporated to dryness. The residue was twice chromatographed over silica gel and was eluted to obtain 1.718 g of 2-desoxy-4-O-[2,4,6-tridesoxy-2,6,bis-(methoxycarbonyl)-amino-3-O-benzyl-α,D-xylohexopyranosyl]-N$^3$-methoxycarbonyl-D-streptamine in the form of a yellow porous mass. Thin-layer chromatography over silica gel with an 80-20-1 chloroform-methanol-ammonium hydroxide eluant yielded an Rf=0.18.

STEP H:

N$^1$-[2(S)-acetyloxy-1-oxo-4-(benzyloxycarbonylamino)-butyl]-2-desoxy-4-O-[2,4,6-tridesoxy-2,6-bis-(methoxycarbonyl)-amino-3-O-benzyl-α,D-xylohexopyranosyl]-N$^3$-methoxycarbonyl-D-streptamine 0.413 ml of triethylamine and 0.256 ml of ethyl chloroformate were added to a solution of 880 mg of (S)α-acetyloxy-γ-N-benzyloxycarbonylamido-n-butyric acid in anhydrous tetrahydrofuran and a solution of 1.362 g of the product of Step G in dimethylformamide was added thereto with stirring. The mixture was stirred for 2 hours and water was added thereto. The mixture was iced for a few hours and was then vacuum filtered. The recovered product was washed and dried to obtain 1.748 g of $N^1$-[2(S)-acetyloxy-1-oxo-4-{benzyloxycarbonylamino}-butyl]-2-desoxy-4-O-[2,4,6-tridesoxy-2,6-bis-(methoxycarbonyl)-amino-3-O-benzyl-α,D-xylohexopyranosyl]-$N^3$-methoxycarbonyl-D-streptamine in the form of white needles melting at 199° C. Thin-layer chromatography over silica gel with a 9-1 chloroform-methanol eluant yielded an Rf=0.34.

STEP I:

1'O-[3-ethoxycarbonylmethylamino)-2-O-benzyl-3,4,6-tridesoxy-α,D-xylohexopyranosyl-(1→6)]-O-[2,4,6-tridesoxy-2,6-bis-(methoxycarbonyl)-amino]-3-O-benzyl-α,D-xylohexopyranosyl-(1→4)]-$N^1$-[2(S)-acetyloxy-1-oxo-4-{benzyloxycarbonylamino}]-butyl-2-desoxy-$N^3$-methoxycarbonyl-D-streptamine A solution of 64.5 ml of anhydrous methylene chloride saturated with hydrobromic acid and 1.42 g of 1-O-acetyl-2-O-benzyl-3-(N-carbethoxy-N-methyl)-amino-3,4,6-tridesoxy-D-xylohexopyranose was stirred at room temperature for 45 minutes and then toluene was added thereto. The mixture was evaporated to dryness and the dry residue was dissolved in 52 ml of methylene chloride. 815 mg of tetraethylammonium bromide, 0.7 ml of diisopropylethylamine and 2.195 g of the product of Step H were added to the mixture which was then refluxed for 4½ hours. Then, 0.5 equivalent of the bromide derivative, 0.5 equivalent of tetraethylammonium bromide and 0.5 equivalent of diisopropylethylamine were added thereto and the mixture was stirred for another 21 hours at reflux. Then, the addition of the said 0.5 equivalents was repeated and the mixture was stirred at reflux for 28 hous. The mixture was poured into methylene chloride and was washed with water and evaporated to dryness to obtain 4.428 g of residue. The latter was chromatographed over silica gel to obtain 2.107 g of pure 1'O-[3-ethoxycarbonylmethylamino)-2-O-benzyl-3,4,6-tridesoxy-α,D-xylohexopyranosyl-(1→6)]-O-[2,4,6-tridesoxy-2,6-bis-(methoxycabonyl)-amino]-3-O-benzyl-α,D-xylohexopyranosyl-(1→4)]-$N^1$-[2(S)-acetyloxy-1-oxo-4-{benzyloxycarbonylamino}]-butyl-2-desoxy-$N^3$-methoxycarbonyl-D-streptamine. Thin-layer chromatography over silica gel with a 6-4 chloroform-acetone eluant yielded an Rf=0.25.

STEP J:

O-[3,4,6-tridesoxy-3-(ethoxycarbonylmethylamino)-2-O-benzyl-α,D-xylohexopyranosyl-(1→6)]-O-[2,4,6-tridesoxy-2,6-bis-(methoxycarbonyl)-amino-3-O-benzyl-α,D-xylohexopyranosyl-(1→4)]-$N^1$-[2(S)-hydroxy-1-oxo-4-(benzyloxycarbonylamino)]-butyl-2-desoxy-$N^3$-(methoxycarbonyl)-D-streptamine 1.1 ml of 2 N sodium hydroxide solution were added to an iced solution of 1.670 g of the product of Step I in 11 ml of methylene chloride and 11 ml of methanol and the mixture was stirred at 0° C. for one hour. The mixture was poured into ice water and was neutralized to a pH of 7 with hydrochloric acid. The mixture was extracted with methylene chloride and the organic phase was washed and evaporated to dryness to obtain 1.566 g of residue. The latter was chromatographed over silica gel to obtain 1.388 g of pure O-[3,4,6-tridesoxy-3-(ethoxycarbonylmethylamino)-2-O-benzyl-α,D-xylohexopyranosyl-(1→6)]-O-[2,4,6-tridesoxy-2,6-bis-(methoxycarbonyl)-amino-3-O-benzyl-α,D-xylohexopyranosyl-(1→4)]-$N^1$-[2(S)-hydroxy-1-oxo-4-(benzyloxycarbonylamino)]-butyl-2-desoxy-$N^3$-(methoxycarbonyl)-D-streptamine in the form of a beige porous mass.

STEP K: Acetate of O-[3,4,6-tridesoxy-3-(ethoxycarbonylmethylamino)-α,D-xylohexopyranosyl-(1→6)]-O-[2,4,6-tridesoxy-2,6-bis-(methoxycarbonyl)-amino-α,D-xylohexopyranosyl-(1→4)]-$N^1$-[4-amino-2(S)-hydroxy-1-oxo]-butyl-2-desoxy-$N^3$-(methoxycarbonyl)-D-streptamine Hydrogen was bubbled through a mixture of 1.365 g of the product of Step J, 275 mg of palladized carbon, 68 ml of acetic acid and 6.8 ml of water for 22 hours and the catalyst was filtered off. The filter was rinsed with acetic acid and the filtrate was evaporated to dryness. The residue was dried under reduced pressure to obtain 1.002 g of acetateof O-[3,4,6-tridesoxy-3-(ethoxycarbonylmethylamino)-α,D-xylohexopyranosyl-(1→6)]-O-[2,4,6-tridesoxy-2,6-bis-(methoxycarbonyl)-amino-α,D-xylohexopyranosyl-(1→4)]-$N^1$-[4-amino-2(S)-hydroxy-1-oxo]-butyl-2-desoxy-$N^3$-(methoxycarbonyl)-D-streptamine in the form of a white solid. Thin-layer chromatography over silica gel with a 70-30-2.5 chloroform-methanol-ammonium hydroxide eluant yielded an Rf=0.17.

STEP L:

O-[2,6-diamino-2,4,6-tridesoxy-α,D-xylohexopyranosyl-[1→4)]-O-[3-methylamino-3,4,6-tridesoxy-α,D-xylohexopyranosyl-(1→6)]-$N^1$-[4-amino-2(S)-hydroxy-1-oxo]-butyl-2-desoxy-D-streptamine 0.980 g of the product of Step K in finely ground form was added with stirring to 4.9 ml of 14 N potassium hydroxide solution in a bath at 65° C. and after 135 mintutes, the mixture was cooled to 0° C. and adjusted to a pH of with sulfuric acid. The resulting yellowish solution was eluted from a column of resin withh 0.4 N ammonium hydroxide to obtain 0.467 g of O-[2,6-diamino-2,4,6-tridesoxy-α,D-xylohexopyranosyl-(1→4)]-O-[3-methylamino-3,4,6-tridesoxy-α,D-xylohexopyranosyl-(1→6)]-$N^1$-[4-amino-2(S)-hydroxy-1-oxo]-butyl-2-desoxy-D-streptamine in the form of a white amorphous powder. Thin-layer chromatography over silica gel with a 2-2-1 chloroform-methanol-ammonium hydroxide eluant yield an Rf=0.14.

NMR Spectrum: ($D_2O$-60 MHz) in hydrochloric acid media

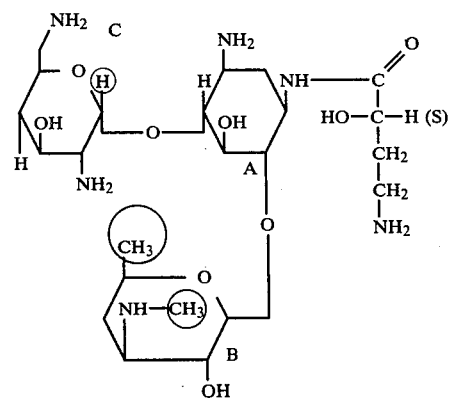

A—$CH_3$ at 1.85 ppm doublet J=6 cps
B—$CH_3$ at 4.1 ppm

C—H anomere at 9.04 ppm doublet J=3 cps

EXAMPLE 4 sulfate of
O-[2,6-diamino-2,4,6-tridesoxy-α,D-xylohexopyrano-syl-(1→4)]-O-[3-methylamino-3,4,6-tridesoxy-α,D-xylohexopyranosyl-(1→6)]-N¹-[4-amino-2(S)-hydroxy-1-oxo]-butyl-2-desoxy-D-streptamine A solution of 350 mg of the product of Example 3 in 20 ml of water was adjusted to a pH of 3 by addition of sulfuric acid and the mixture was concentrated and filtered. The filtrate was further concentrated and was then poured with stirring into methanol. The mixture was iced and filtered to obtain 481 mg of sulfate of O-[2,6-diamino-2,4,6-tridesoxy-α,D-xylohexopyrano-syl-(1→4)]-O-[3-methylamino-3,4,6-tridesoxy-α,D-xylohexopyranosyl-(1→6)]-N¹-[4-amino-2(S)-hydroxy-1-oxo]-butyl-2-desoxy-D-streptamine in the form of a white amorphous product. Thin-layer chromatography over silica gel with a 2-2-1 chloroform-methanol-ammonium hydroxide eluant yielded an Rf=0.14.

NMR Spectrum (D$_2$O-60 MHz):

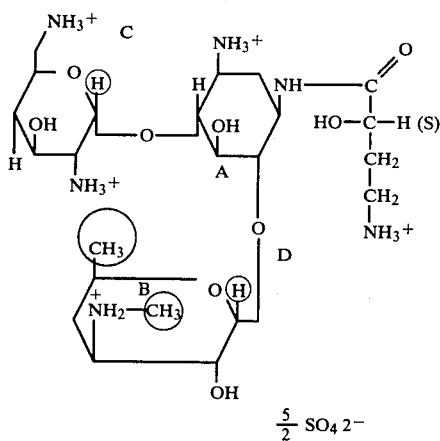

A—1.2 ppm doublet J=6
B—2.6 ppm
C—H anomere 6.1 ppm doublet J=3.5
D—H anomere 5.2 ppm doublet J=3.5

EXAMPLE 5

O-[2,6-diamino-2,3,4,6-tetradesoxy-α,D-erythrohex-opyranosyl-(1→4)]-O-[3,4,6-tridesoxy-3-methylamino-α,D-xylohexopyranosyl-(1→6)]-N¹-(4-amino-2(S)-hydroxy-1-oxo)-butyl-2-desoxy-D-strepamine

STEP A:

1,6-N,O-(carbonyl)-2-desoxy-4-O-[2,3,4,6-tetradesoxy-2,6-bis-[methoxycarbonylamino]-α,D-erythrohex-opyranosyl]-N³-methoxycarbonyl-D-streptamine A solution of 20 g of 3′,4′-didesoxy-tetra-N-carbomethoxy-neamine (prepared as in French Pat. No. 2,263,745) in 180 ml of dimythylformamide in the presence of tert.-butanol and potassium tert.-butanol was stirred with cooling while 5.5 g of sodium hydride as a 50% oil suspension were slowly added thereto and after stirring the mixture for 21 hours, excess sodium hydride was destroyed by acetic acid addition. Water and added thereto and the mixture was evaporated to dryness. The residue was taken up in a chloroform-ethanol mixture and the mixture was filtered. The filtrate was evaporated to dryness to obtain 30 g of 1,6-N,O-(carbonyl)-2-desoxy-4-O-[2,3,4,6-tetradesoxy-2,6-bis-[methoxycarbonylamino]-α,D-erythrohexopyranosyl]-N³-methoxycarbonyl-D-streptamine as a syrup which was used as is for the next step.

STEP B:

2-desoxy-4-O[2,3,4,6-tetradesoxy-2,6-bis-[methoxycarbonylamino]-α,D-erythrohexopyranosyl]-N³-methoxycarbonyl-D-streptamine The syrup of Step A was added to equal volumes of N sodium hydroxide and oxygenated water and after stirring the mixture for 5 hours, excess peroxide was destroyed by addition of sodium thiosulfate. The pHof the mixture was adjusted to 7 with concentrated sulfuric acid and the mixture was evaporated to dryness. The residue was taken up in a 9-1 chloroform-methanol mixture and the mixture was filtered. The filtrate was evaporated to dryness and the residue was chromatographed over silica gel to obtain 8.1 g of 2-desoxy-4-O-[2,3,4,6-tetradesoxy-2,6-bis-[methoxycarbonylamino]-α,D-erthyrohexopyranosyl]-N³-methoxycarbonyl-D-streptamine. Thin-layer chromatography over silica gel with an 80-20-1 chloroform-methanol-ammonium hydroxide eluant yielded an Rf=0.12.

STEP C:

2-desoxy-4-O-[2,3,4,6-tetradesoxy-2,6-bis-[methoxycarbonylamino]-α,D-xylohexopyranosyl]-N¹-[2(S)-acetyloxy-1-oxo-4-(benzyloxycarbonylamino)-butyl]-N³-methoxycarbonyl-D-streptamine 1.39 ml of triethanolamine, 0.9 ml of ethyl orthoformate and 3.715 gm of the product of Step B dissolved in dimethylformamide were added to a solution of 2.95 g of (S)-α-acetyloxy-γ-N-benzyloxy-carbonylamido-N-butyric acid in tetrahydrofuran and the mixture was stirred for one hour and was poured into iced water. The mixture was extracted with chloroform and the organic extracts was washed with water, filtered and evaporated to dryness. The residue was chromatographed over silica gel to obtain 4.75 g of 2-desoxy-4-O-[2,3,4,6-tetradesoxy-2,6-bis-[methoxycarbonylamino]-α,D-xylohexopyranosyl]-N¹-[2(S)-acetyloxy-1-oxo-4-(benzyloxycarbonylamino)-butyl]-N³-methoxycarbonyl-D-streptamine. Thin-layer chromatography over silica gel with a 95-5 chloroform-methanol eluant yielded an Rf=0.15.

STEP D:

O-[2,6-dimethoxycarbonylamino-2,3,4,6-tetradesoxy-α,D-erythrohexopyranosyl-(1→4)]-O-[3,4,6-tridesoxy-3-ethoxycarbonylmethylamino-2-O-benzyl-α,D-xylohexopyranosyl-(1→6)]-N¹-[2(S)-acetyloxy-1-oxo-4-(benzyloxycarbonylamino)]-butyl-2-desoxy-N³-methoxycarbonyl-D-streptamine A solution of 4.14 g of 1-O-acetyl-2-O-benzyl-3-(N-carbethoxy-N-methyl)-amino-3,4,6-tridesoxy-D-xylohexopyranose in methylene chloride saturated with hydrogen bromide was stirred and was evaporated to dryness and the residue was taken up in methylene chloride. 1.92 ml of diisopropylethylamine, 2.38 g of tetraethylammonium bromide and 45 g of the product of Step C were added to the mixture which was then refluxed for 21½ hours. The mixture was diluted with methylene chloride and the organic phase was washed twice with water, was dried, filtered and evaporated to dryness. The residue was chromatographed over silica gel to obtain 32.35 g of pure O-[2,6-dimethoxycarbonylamino-2,3,4,6-tetradesoxy-α,D-erythrohexopyranosyl-(1→4)]-O-[3,4,6-tridesoxy-3-ethoxycarbonylmethylamino-2-O-benzyl-α,D-xylohexopyranosyl-(1→6)]-$N^1$-[2(S)-acetyloxy-1-oxo-4-(benzyloxycarbonylamino)]-butyl-2-desoxy-$N^3$-methoxycarbonyl-D-streptamine. Thin-layer chromatography over silica gel with a 7-3 chloroform-acetone yielded an Rf=0.16.

STEP E:
O-[3-ethoxycarbonylmethylamino-2-O-benzyl-3,4,6-tridesoxy-α,D-xylohexopyranosyl-(1→6)]-O-[2,6-bis-(methoxycarbonylamino)-2,3,4,6-tetradesoxy-α,D-erythrohexopyranosyl-(1→4)]-$N^1$-[2(S)-hydroxy-1-oxo-4-(benzyloxycarbonylamino)]-butyl-2-desoxy-$N^3$-methoxycarbonyl-D-streptamine 2 N sodium hydroxide was added to a solution of 15.2 g of the compound of Step D in a methylene chloride-methanol mixture cooled to 0° C. and the mixture was stirred for one hour and was then neutralized with hydrochloric acid. The mixture was extracted with methylene chloride and the organic phase was washed, dried, filtered and evaporated to dryness to obtain 14.6 g of O-[3-ethoxycarbonylmethylamino-2-O-benzyl-3,4,6-tridesoxy-α,D-xylohexopyranosyl-(1→6)]-O-[2,6-bis-(methoxycarbonylamino)-2,3,4,6-tetradesoxy-α,D-erythrohexopyranosyl-(1→4)]-$N^1$-[2(S)-hydroxy-1-oxo-4-(benzyloxycarbonylamino)]-butyl-2-desoxy-$N^3$-methoxycarbonyl-D-streptamine. Thin-layer chromatography over silica gel with a 65-35 chloroform-methanol eluant yielded an Rf=0.12.

STEP F: Acetate of
O-[3-ethoxycarbonylmethylamino-3,4,6-tridesoxy-α,D-xylohexopyranosyl-(1→6)]-O-[2,6-bis-(methoxycarbonyl)-amino-2,3,4,6-tetradesoxy-α,D-erythrohexopyranosyl-(1→4)]-$N^1$-[2(S)-hydroxy-1-oxo-4-amino]-butyl-2-desoxy-$N^3$-methoxycarbonyl-D-streptamine Hydrogen was bubbled through a mixture of 14.6 g of the compound of Step E, a mixture of 10 parts of acetic acid and water and 3.1 g of 10% palladized charcoal for 16 hours and the mixture was filtered. The filter was washed and the filtrate was evaporated to dryness. The product was dried to obtain 11.7 g of acetate of O-[3-ethoxycarbonylmethylamino-3,4,6-tridesoxy-α,D-xylohexopyranosyl-(1→6)]-O-[2,6-bis-(methoxycarbonyl)-amino-2,3,4,6-tetradesoxy-α,D-erythrohexopyranosyl-(1→4)]-$N^1$-[2(S)-hydroxy-1-oxo-4-amino]-butyl-2-desoxy-$N^3$-methoxycarbonyl-D-streptamine. Thin-layer chromatography over silica gel with a 80-20-2 chloroform-methanol-ammonium hydroxide eluant yielded an Rf=0.33.

STEP G:
O-[2,6-diamino-2,3,4,6-tetradesoxy-α,D-erythrohexopyranosyl-(1→4)]-O-[3,4,6-tridesoxy-3-methylamino-α,D-xylohexopyranosyl-(1→6)]-$N^1$-[4-amino-2(S)-hydroxy-1-oxo]-butyl-2-desoxy-D-streptamine A mixture of 8 ml of 14 N potassium hydroxide solution and 11.7 g of the product of Step F was stirred with heating for 9 hours and was then cooled and neutralized with N sulfuric acid. The product was chromatographed over a resin column with an ammonium hydroxide eluant to obtain 10.35 g of O-[2,6-diamino-2,3,4,6-tetradesoxy-α,D-erythrohexopyranosyl-(1→4)]-O-[3,4,6-tridesoxy-3-methylamino-α,D-xylohexopyranosyl-(1→6)]-$N^1$-[4-amino-2(S)-hydroxy-1-oxo]-butyl-2-desoxy-D-streptamine. Thin-layer chromatography over silica gel with a 2-2-1 chloroform-methanol-ammonium hydroxide eluant yielded an Rf=0.27.

NMR Spectrum ($D_2O$-60 MHz):

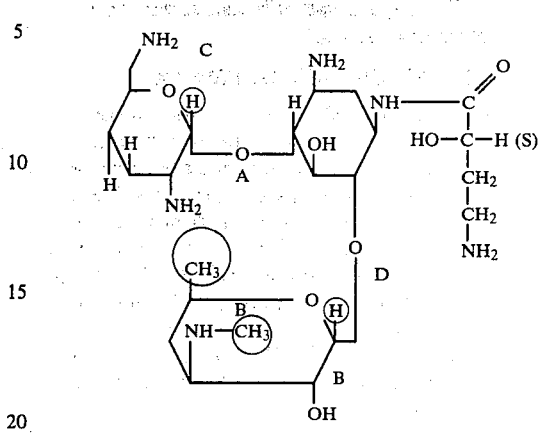

A—$CH_3$—1.2 ppm doublet J=6
B—$CH_3$—2.7 ppm
C—H anomere—5.8 ppm doublet J=3.5
D—H anomere—5.1 ppm doublet J=3

EXAMPLE 6
Sulfate of O-[2,6-diamino-2,3,4,6-tetradesoxy-α,D-erythrohexopyranosyl-(1→4)]-O-[3,4,6-tridesoxy-3-methylamino-α,D-xylohexopyranosyl-(1→6)]-$N^1$-[2(S)-hydroxy-1-oxo-4-amino]-butyl-2-desoxy-D-streptamine A solution of the product of Example 5 in 10 ml of water was adjusted to a pH of 3 by addition of 0.1 N sulfuric acid and the mixture was then concentrated and filtered. The recovered product was crystallized from methanol at 0° C. and the mixture was vacuum filtered. The product was washed and dried to obtain 14 g of sulfate of O-[2,6-diamino-2,3,4,6-tetradesoxy-α,D-erythrohexopyranosyl-(1→4)]-O-[3,4,6-tridesoxy-3-methylamino-α,D-xylohexopyranosyl-(1→6)]-$N^1$-[2(S)-hydroxy-1-oxo-4-amino]-butyl-2-desoxy-D-streptamine. Thin-layer chromatography over silica gel with a 2-2-1 chloroform-methanol-ammonium hydroxide eluant yielded an Rf=0.25.

NMR Spectrum ($D_2O$-60 MHz):

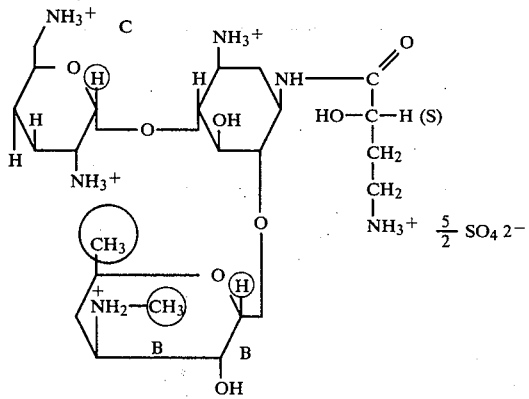

A—$CH_3$ 1.2 ppm doublet J=4
B—$CH_3$ 2.7 ppm
C—H anomere—5.9 ppm doublet J=4
D—H anomere—5.1 ppm doublet J=9.5

EXAMPLE 7

An injectable solution was prepared with 50 mg of the product of Example 2 and sufficient sterile water to obtain a final volume of 1 ml.

PHARMACOLOGICAL DATA

The in vitro antibacterial activity of the compounds of Examples 2,4 and 6 was determined by a dilution method in liquid media. A series of tubes were prepared with each receiving the same quantity of nutritive medium and increasing quantities of the test product were distributed to each tube which were then seeded with a bacterial strain. After incubating 18, 24 or 48 hours at 37° C. in an oven, the inhibition of bacterial growth was determined by transillumination to determine the minimum inhibiting concentration (MIC) of the product expressed in μg/ml of base. The results are reported in the following Tables.

| PRODUCT OF EXAMPLE 2 | | | |
|---|---|---|---|
| | Reading After | | |
| STRAINS | 18 h. | 24 h. | 48 h. |
| Staphylococcus aureus ATCC 6538 P.S. | 0,2 | 0,5 | 1 |
| Staphylococcus aureus U.C.1128 P.R. | 0,2–0,5 | 0,5 | 1 |
| Staphylococcus aureus Exp.N°54146 | 0,2 | 1 | 2 |
| Staphylococcus aureus Co 15 R cephalexine | 0,1 | 0,2 | 0,5 |
| Streptococcus pyogenes A 561 | 0,5 | 0,5 | 1 |
| Bacillus subtilis ATCC 6633 | 10 | 20 | 40 |
| Escherichia Coli ST ATCC 9637 | 0,5 | 0,5 | 1 |
| Escherichia Coli RT ATCC 11303 | 0,5 | 0,5 | 1 |
| Escherichia Coli Exp.T $O_{26}B_6$ | 0,5 | 1 | 1 |
| Escherichia Coli RG R 55 123 D | 0,5 | 0,5 | 0,5 |
| Klebsiella pneumoniae Exp.52145 | 0,1 | 0,1 | 0,1 |
| Klebsiella pneumoniae 2536 R | 0,2 | 0,2 | 0,2 |
| Proteus mir. (indol−) A 235 | 2 | 2 | 3 |
| Proteus vulgaris (indol+) A 232 | 2 | 3 | 3 |
| Enterobacter cloacae 681 | 0,1 | 0,2 | 0,2 |
| Providencia Du 48 | 3 | 5 | 5 |
| Pseudomonas 3935 Exp. SG | 1 | 1 | 2 |
| Pseudomonas 8951 RGT | 3 | 20 | >40 |
| Serratia RG 2532 | 0,5 | 0,5 | 1 |

| PRODUCT OF EXAMPLE 4 | | | |
|---|---|---|---|
| | Reading After | | |
| STRAINS | 18 h. | 24 h. | 48 h. |
| Staphylococcus aureus ATCC 6538 P.S. | 1 | 1 | 2 |
| Staphylococcus aureus U.C.1128 P.R. | 0,2–0,5 | 0,5 | 1 |
| Staphylococcus aureus Exp.N°54146 | 0,5 | 1 | 2 |
| Staphylococcus aureus Co 15 R cephalexine | 0,5 | 0,5 | 2 |
| Streptococcus pyogenes A 561 | 0,5 | 1 | 1,5 |
| Bacillus subtilis ATCC 6633 | 0,1 | 0,2 | 0,5 |
| Escherichia Coli ST ATCC 9637 | 1 | 2 | 2 |
| Escherichia Coli RT ATCC 11303 | 0,5 | 0,5 | 2 |
| Escherichia Coli Exp.T $O_{26}B_6$ | 1 | 1 | 2 |
| Escherichia Coli RG R 55 123 D | 0,5 | 0,5 | 1 |
| Klebsiella pneumoniae Exp.52145 | 0,2 | 0,2 | 0,5 |
| Klebsiella pneumoniae 2536 R | 0,2 | 0,2 | 0,5 |
| Proteus mir. (indol−) A 235 | 3 | 5 | 5 |
| Proteus vulgaris (indol+) A 232 | 3 | 10 | 20 |
| Enterobacter cloacae 681 | 0,5 | 0,5 | 0,5 |
| Providencia Du 48 | 20 | 40 | 40 |
| Pseudomonas 3935 Exp.SG | 2 | 2 | 5 |
| Pseudomonas 8951 RGT | 1 | 1 | 3 |
| Serratia RG 2532 | 1 | 1 | 2 |

| PRODUCT OF EXAMPLE 6 | | | |
|---|---|---|---|
| | Reading After | | |
| STRAINS | 18 h. | 24 h. | 48 h. |
| Staphylococcus aureus ATCC 6538 P.S. | 0,5 | 0,5 | 1 |
| Staphylococcus aureus U.C.1128 P.R. | 0,5 | 0,5 | 1 |
| Staphylococcus aureus Exp.N°54146 | 0,2 | 2 | 5 |
| Staphylococcus aureus Co 15 R cephalexine | 0,1 | 0,2 | 0,5 |
| Streptococcus pyogenes A 561 | 1 | 2 | 3 |
| Bacillus subtilis ATCC 6633 | 0,05 | 0,05 | 0,2 |
| Escherichia Coli ST ATCC 9637 | 1 | 1 | 1 |
| Escherichia Coli RT ATCC 11303 | 0,5 | 0,5 | 1 |
| Escherichia Coli Exp.T $O_{26}B_6$ | 1 | 1 | 1 |
| Escherichia Coli RG R 55 123 D | 0,5 | 0,5 | 0,5 |
| Klebsiella pneumoniae Exp.52145 | 0,1 | 0,1 | 0,1 |
| Klebsiella pneumoniae 2536 R | 0,2 | 0,2 | 0,5 |
| Proteus mir. (indol−) A 235 | 2 | 3 | 5 |
| Proteus vulgaris (indol+) A 232 | 1 | 2 | 2 |
| Enterobacter cloacae 681 | 0,2 | 0,2 | 0,2 |
| Providencia Du 48 | 3 | 5 | 20 |
| Pseudomonas 3935 Exp. SG | 1 | 1 | 2 |
| Pseudomonas 8951 RGT | 1 | 2 | 2 |
| Serratia RG 2532 | 0,5 | 0,5 | 1 |

The results of the above Tables show that the tested compounds have a good antibacterial activity.

Various modifications of the products and methods of the invention may be made without departing from the spirit or scope thereof and it is to be understood that the invention is intended to be limited only as defined in the appended claims.

We claim:

1. A compound selected from the group consisting of desoxystreptamines of the formula

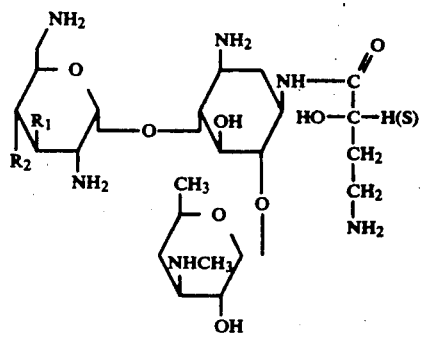

wherein $R_1$ and $R_2$ are selected from the group consisting of hydrogen and hydroxyl with at least one of them being hydrogen and their non-toxic, pharmaceutically acceptable acid addition salts.

2. A compound of claim 1 selected from the group consisting of 1' O-[2,6-diamino-2,3,6-tridesoxy-α,D-ribohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

3. A compound of claim 1 selected from the group consisting of 1' O-[2,6-diamino-2,4,6-tridesoxy-α,D-xylohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

4. A compound of claim 1 selected from the group consisting of 1' O-[2,6-diamino-2,3,4,6-tetradesoxy-α,D-erythrohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

5. A compound selected from the group consisting of

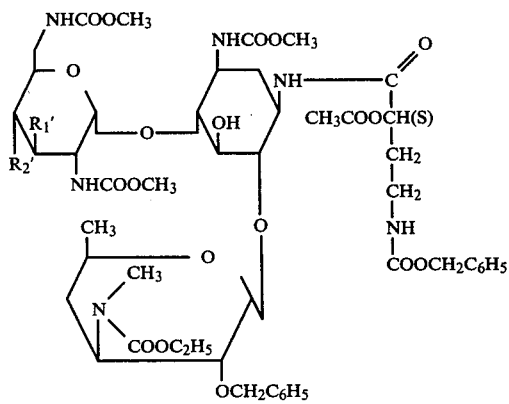

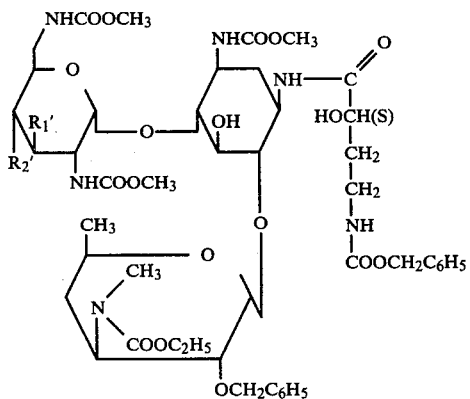

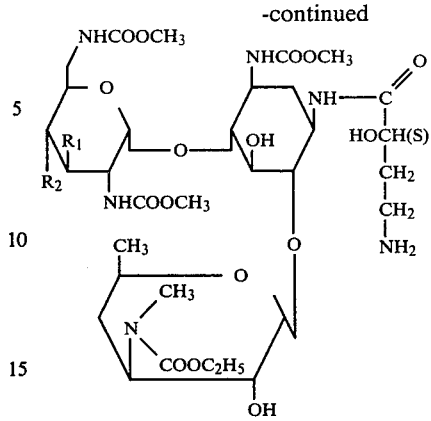

wherein $R_1'$ and $R_2'$ are selected from the group consisting of hydrogen and benzoxy with at least one being hydrogen and $R_1$ and $R_2$ are selected from the group consisting of hydrogen and hydroxy with at least one being hydrogen.

6. An antibiotic composition comprising an antibiotically effective amount of at least one compound of claim 1 and an excipient.

7. A composition of claim 6 selected from the group consisting of 1' O-[2,6-diamino-2,3,6-tridesoxy-α,D-ribohexopyranosyl-(1→4)]-O-[3-methylamino-3,4,6-tridesoxy-α,D-xylohexopyranosyl-(1→6)]-N¹-[2(S)-hydroxy-1-oxo-4-amino]butyl-2-desoxy-D-streptamine and its sulfate.

8. A composition of claim 6 selected from the group consisting of 1' O-[2,6-diamino-2,4,6-tridesoxy-α,D-xylohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

9. A composition of claim 6 selected from the group consisting of 1' O-[2,6-diamino-2,3,4,6-tetradesoxy-α,D-erythrohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

10. A method of treating bacterial infections in warm-blooded animals comprising administering to warm-blooded animals a bactericidally effective amount of at least one compound of claim 1.

11. A method of claim 10 wherein the compound is selected from the group consisting of 1' O-[2,6-diamino-2,3,6-tridesoxy-α,D-ribohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

12. A method of claim 10 wherein the compound is selected from the group consisting of 1' O-[2,6-diamino-2,4,6-tridesoxy-α,D-xylohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

13. A method of claim 10 wherein the compound is selected from the group consisting of 1' O-[2,6-diamino-2,3-4,6-tetradesoxy-α,D-erythrohexopyranosyl-(1→4)]-O-[3-methylamino-3,4,6-tridesoxy-α,D-xylohexopyranosyl-(1→6)]-N¹-[2(S)-hydroxy-1-oxo-4-amino]-butyl-2-desoxy-D-streptamine and its sulfate.

* * * * *

UNITED STATES PATENT AND TRADEMARK OFFICE
CERTIFICATE OF CORRECTION

PATENT NO. : 4,242,331

DATED : December 30, 1980

INVENTOR(S) : JEAN-CLAUDE GASC ET AL.

Page 1 of 2

It is certified that error appears in the above—identified patent and that said Letters Patent is hereby corrected as shown below:

Column 4, lines 6 and 7: "IV and IV" should read
-- IV and IV' --.

Column 8, line 2: "O-[3-ethoxy ..." should read
-- O-[3-(ethoxy ... --.

line 7: "(benzyloxycarbonylamino]" should read
-- (benzyloxycarbonylamino)] --.

Column 14, line 38: "withh" should read -- with --.

Column 15, line 64: "Water and added" should read
-- Water was added --.

Column 18, Example 6: The portion of the structural formula which reads

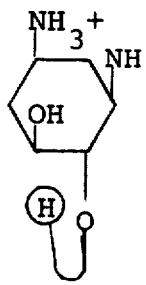

UNITED STATES PATENT AND TRADEMARK OFFICE
CERTIFICATE OF CORRECTION

PATENT NO. : 4,242,331   Page 2 of 2
DATED : December 30, 1980
INVENTOR(S) : JEAN-CLAUDE GASC ET AL.

It is certified that error appears in the above—identified patent and that said Letters Patent is hereby corrected as shown below:

should read

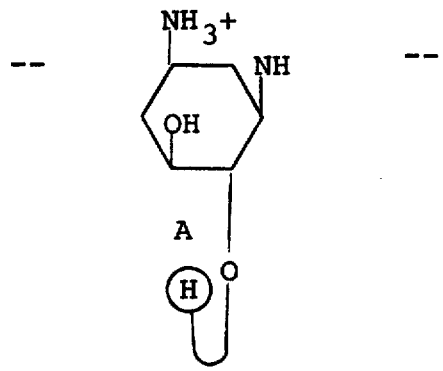

Signed and Sealed this

Sixteenth Day of June 1981

[SEAL]

Attest:

RENE D. TEGTMEYER

Attesting Officer    Acting Commissioner of Patents and Trademarks